(12) United States Patent
Tihon

(10) Patent No.: US 6,358,229 B1
(45) Date of Patent: *Mar. 19, 2002

(54) URINARY DRAIN

(75) Inventor: Claude Tihon, Eden Prairie, MN (US)

(73) Assignee: ContiCare Medical, Inc., Eden Prairie, MN (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 194 days.

(21) Appl. No.: 09/024,732

(22) Filed: Feb. 17, 1998

(51) Int. Cl.[7] ............................................. A61M 5/178
(52) U.S. Cl. ........................... 604/170.03; 604/170.02; 604/164.01
(58) Field of Search ............................ 604/48, 73, 93, 604/164, 165, 257, 264, 265, 280, 281, 282, 317, 349, 8, 170, 523, 524–525, 530, 533, 528, 534, 535, 164.01, 164.02, 164.03, 164.07, 164.13, 165.01, 165.02, 170.01, 170.02, 170.03

(56) References Cited

U.S. PATENT DOCUMENTS

| | | | | |
|---|---|---|---|---|
| 3,860,006 A | * | 1/1975 | Patel | 128/347 |
| 4,236,520 A | * | 12/1980 | Anderson | 128/348 |
| 4,643,716 A | * | 2/1987 | Drach | 604/8 |
| 4,713,049 A | * | 12/1987 | Carter | 604/8 |
| 4,950,228 A | * | 8/1990 | Knapp, Jr. et al. | 604/8 |
| 5,354,263 A | * | 10/1994 | Coll | 604/8 |
| 5,364,340 A | * | 11/1994 | Coll | 604/8 |
| 5,391,155 A | * | 2/1995 | Sachse | 604/170 |
| 5,407,435 A | * | 4/1995 | Sachse | 604/170 |
| 5,523,092 A | * | 6/1996 | Hansom et al. | 424/423 |
| 5,647,843 A | * | 7/1997 | Mesrobian et al. | 604/8 |
| 5,681,274 A | * | 10/1997 | Perkins et al. | 604/8 |
| 5,702,372 A | * | 12/1997 | Nelson | 604/264 |
| 5,749,826 A | * | 5/1998 | Faulkner | 600/29 |
| 5,776,115 A | * | 7/1998 | Antonshkiw et al. | 604/282 |
| 5,800,407 A | * | 9/1998 | Eldor | 604/264 |
| 5,814,029 A | * | 9/1998 | Hassett | 604/281 |
| 5,871,470 A | * | 2/1999 | McWha | 604/158 |
| 5,879,333 A | * | 3/1999 | Smith | 604/164 |
| 5,885,217 A | * | 3/1999 | Gisselberg et al. | 600/434 |
| 5,919,172 A | * | 7/1999 | Golba, Jr. | 604/272 |
| 5,921,952 A | * | 7/1999 | Desmond, III et al. | 604/8 |

\* cited by examiner

Primary Examiner—Richard K. Seidel
Assistant Examiner—LoAn H. Thanh
(74) Attorney, Agent, or Firm—Nikolai & Mersereau, P.A.

(57) ABSTRACT

A urinary drain device comprising an elongated flexible tube member whose distal end portion is preformed so as to assume a coiled configuration when unconstrained. The distal end portion also includes one or more openings through its side wall through which urine may enter and flow. A stiffening member in the form of a semi-rigid tube having an open distal end leading to its lumen is designed to be inserted into the lumen of the tubular drain body member to thereby straighten the coil during insertion and removal. Urine entering the distal end portion of the drain body member may flow through the open end of the tubular stiffener and, thence, through the lumen of the tubular stiffener to provide an indication to a medical attendant that the distal end portion of the drain body member has been advanced to the point that it is resident within the urinary bladder. Removal, now, of the tubular stiffener allows the distal end portion to revert back to a coiled condition for retaining the urinary drain device in place.

8 Claims, 1 Drawing Sheet

URINARY DRAIN

BACKGROUND OF THE INVENTION

I. Field of the Invention

This invention relates generally to a catheter device for draining the urinary bladder, and more particularly to a bladder drainage catheter having an improved retention device integrally formed thereon.

II. Discussion of the Prior Art

The most common bladder drainage catheter in current use is the so-called Foley catheter. It comprises an elongated, double-lumen catheter where one lumen is open at a distal end thereof, providing a urine flow path through that lumen when the distal end is inserted through the urethra of a patient and into his/her urinary bladder. The second lumen leads from the proximal end of the catheter to an inflation port passing through the wall of the catheter body near its distal end and which is subtended by an expandable retention device. By injecting saline or other suitable fluid through the second lumen, the retention device is inflated within the bladder to a size precluding passage back down through the urethra.

One problem that quite frequently arises with the use of Foley catheters is that patients who may be semi-conscious due to pain relieving drugs and who find the catheter irritating, may try to extract it without help and without first deflating the retention balloon. This can result in severe trauma to the urethral lining. Another deficiency of the Foley catheter is that, at times, the retention balloon is inflated before the balloon reaches the bladder. This can result in severe damage to the urethra. No such premature inflation of a balloon in a urethra is possible with the present invention in that the retention device does not utilize a balloon.

When the prior art Foley catheter is used in male patients and is left in place over prolonged time periods, there is no provision for collecting and draining excretions from the prostate gland. The catheter body blocks the secretions from the prostate gland and this can lead to prostatitis and feeling of irritation and pain by the patient. The lack of regular irrigation of the prostatic urethra may also lead to urethritis.

A need, therefore, exists for a urinary drain that is comfortable when installed and that is retained in place against nominal pulling forces tending to extract it, but which can be removed without undue trauma to the neck of the bladder and the urethral lining, and which does not involve an inflatable balloon.

Also, a bladder drainage catheter for use in male patients should make provision for collection and drainage of prostatic fluids.

SUMMARY OF THE INVENTION

To obviate the aforementioned drawbacks of the prior art bladder drainage catheter, I have developed a urinary drain apparatus that comprises as a first element thereof an elongated, flexible, tubular member having a proximal end, a distal end and a lumen extending therebetween. The tubular member has an outer diameter permitting passage through a patient's urethra and is of a length such that placement of a distal end portion into the patient's urinary bladder will leave a proximal end portion of the tubular member extending beyond the urethral meatus. The distal end portion of the tubular member is preformed so that when unconstrained it forms a bladder retention coil that extends laterally from a longitudinal axis of the tubular member. The distal end portion further includes one or more apertures extending from a periphery of the tubular body member to the lumen through which urine may flow. To assist in placement and subsequent removal of the urinary drain, there is provided a tubular stiffening device that is dimensioned to be insertable into the lumen of the tubular drain member and is of a length so that when fully inserted, the bladder retention coil proximate the distal end thereof is straightened, the tubular stiffening device has an open distal end and an internal lumen for permitting urine flow therethrough. During placement, a trickle of urine out from the proximal end of the stiffening member serves to provide an indication that the distal end portion of the tubular body member has been inserted into the patient's urinary bladder. Subsequent removal of the tubular stiffening member from the lumen of the tubular drain member allows the distal end portion thereof to reform the bladder retention coil.

By proper attention to the durometer of the tubular body member proximate its distal end portion and the manner in which it may be heat treated to induce the memory property causing the curl to form, the amount of force needed to extract the drain once it has been installed can be tailored so that pulling forces of a nominal amount, such as may be caused by normal body movements, will not result in the catheter pulling out from the patient. However, where more than nominal force is applied at the proximal end of the drain body, the drain body can be extracted without any appreciable injury to the urinary tract even though the tubular stiffening member is not reinserted for the purpose of straightening the curl before removal.

Furthermore, in accordance with the present invention, drainage apertures are provided through the wall of the drain body in a zone designed to span the prostate gland of a male patient when the distal end portion is resident within the urinary bladder and in its curl configuration. Hence, any exudate from the prostate gland can pass through the drain.

DESCRIPTION OF THE DRAWINGS

The foregoing features, objects and advantages of the invention will become apparent to those skilled in the art from the following detailed description of a preferred embodiment, especially when considered in conjunction with the accompanying drawings in which like numerals in the several views refer to corresponding parts.

DESCRIPTION OF THE PREFERRED EMBODIMENT

Figure 1:
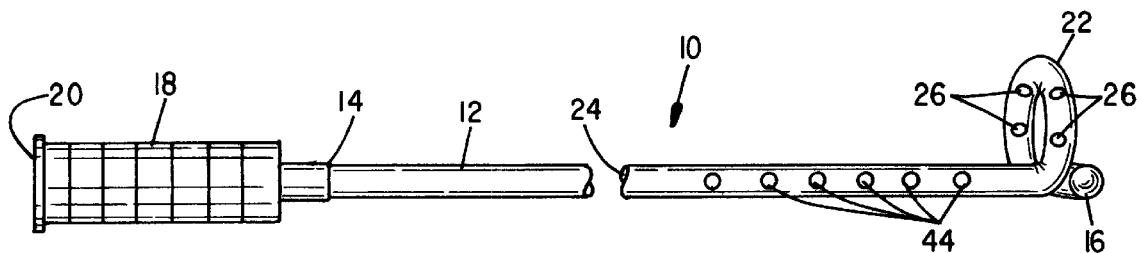
FIG. 1 is a perspective view of the drainage catheter comprising a preferred embodiment of the present invention.

Referring to FIG. 1, there is indicated generally by numeral 10 a urinary drain catheter. It is seen to comprise an elongated flexible plastic tubular drain body 12 having a proximal end 14 and a distal end 16. Affixed to the proximal end 14 is a molded plastic hub 18 having a standard fitting 20 to receive a standard urine collection bag and connecting tubing. The length of the tubular drain body member 12 may vary depending upon whether it is to be used with male, female or juvenile patients and may typically have an outer diameter in a range from about 14–24 Fr for normal adults, allowing it to be readily inserted through the urethral meatus and through the urethra until the distal end portion is disposed within the urinary bladder. The flexible tubular drain body 12 may typically have a durometer in the range from about 35 to 90, Shore A. Polyurethane, polyethylene or silicon rubber are suitable plastics.

The distal end portion is preformed at the time of manufacture so as to exhibit a memory property which results in the formation of a loop or curl identified 22 when the device is unconstrained. The curl may be imparted by inserting the distal end portion of the plastic drain body 12 into an appropriately shaped mold and then heating the mold above the crystallization temperature of the plastic from which the drain body is formed.

Formed through the wall of the tubular drain body member 12 and leading to its internal lumen 24 are one or more apertures, as at 26, through which urine collected in the bladder may flow. It is to be especially noted that the distal end 16 of the urinary drain catheter tubular drain body 12 is closed.

Figure 2:
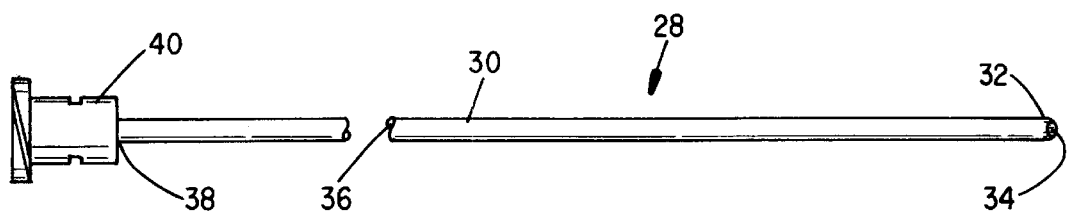
FIG. 2 is a side elevational view of a tubular stiffening device to be used with the drainage catheter of FIG. 1.

Referring next to FIG. 2, there is illustrated a side view of a tubular stiffening member 28 that is used to facilitate insertion and removal of the drainage catheter 10 from a patient's urinary tract. It comprises an elongated tube 30, made of either metal or plastic, and which is semi-rigid compared to the tubular drain body 12. It has a distal end 32 with an opening 34 therethrough leading to its internal lumen 36 that extends the full length of the tubular stiffener 28. Affixed to a proximal end 38 of the stiffener 28 is a molded plastic hub 40 that is designed to mate and lock with the Luer fitting 20 of the hub 18 of the urinary drain device 10.

Figure 3:
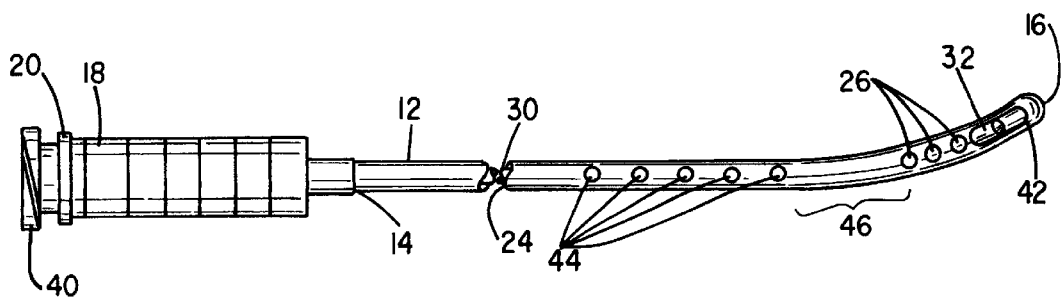
FIG. 3 is a side elevational view of the drainage catheter of FIG. 1 with the tubular stiffening device of FIG. 2 inserted therein.

FIG. 3 shows the configuration of the composite assembly when the stiffening member 28 of FIG. 2 is inserted into the lumen 24 of the tubular drain body 12 and when the respective hubs 40 and 18 thereof are locked together. The stiffening member 30 is of sufficient rigidity to uncoil the curl 22 when so inserted. The distal tip 32 of the stiffening member can be seen through the eyelet opening 42 formed through the side wall of the tubular drain body member 12. This eyelet opening 42 is hidden from view in FIG. 1 because of the curl configuration of the distal end portion of the drain catheter body.

When the drainage catheter of the present invention is intended for use with adult male patients, it has been found expedient to include one or more apertures, as at 44, through the wall of the drain body 12 and leading to the lumen 24 in a zone that will be adjacent the prostate gland when the curled portion of the device is resident within the urinary bladder. This permits the collection and elimination of fluids secreted by the prostate gland.

It is to be further noted from FIG. 3 that in a zone identified by bracket 46, the catheter's tubular drain body is free of apertures and relatively smooth. When the drain body is appropriately installed in a patient (male or female), the zone 46 spans the bladder neck region when the distal end portion forming curl 22 of the tubular drain body 12 is resident within the patient's bladder. Being free of such apertures, the zone 46 is quite smooth and, therefore, non-irritating.

In use, the assembly of FIG. 3 is provided in a sterile package and the distal end portion will typically be coated with a suitable lubricant, such as a water soluble jelly or the like. Because the distal end 16 of the tubular drain body 12 is closed, the lubricant is prevented from entering the lumen and thereby potentially occluding the opening 34 formed in the distal end of the stiffening member 28.

The device is removed from its sterile pack and then the distal end 16 is inserted through the urethral meatus and advanced through the urethra until a trickle of urine is detected exiting the proximal end of the hub 40. At this point, the medical attendant will know that the distal end portion has passed distally beyond the urinary sphincter and is resident in the urinary bladder. At this point, the attendant unlocks the coupling between hub 18 and hub 40 and strips out the stiffening member 28 from the lumen 24 of the drain catheter 10. Being no longer reinforced and constrained by the stiffening member 28, the distal end portion reverts to its curled condition, such as shown in FIG. 1, with the curl serving to retain the drain in place within the patient's urinary tract.

When it is desired to remove the drain from the patient, the medical attendant may reinsert the stiffening member through the lumen of the drain body 12, again causing the curl to straighten out so that it may more readily be withdrawn down the urethra.

As earlier mentioned, even when no stiffening member is used, the drain catheter 10 may still be removed from the patient because the tip portion is sufficiently soft and deformable to allow its withdrawal without significant trauma to the bladder neck or the urethral lining.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself.

What is claimed is:

1. A urethral drain apparatus, comprising:

an elongated, flexible, tubular drain body member having a proximal end, a closed distal end and a lumen extending therebetween, the tubular drain body member having an outer diameter adapted for passage through a patient's urethra and of a length such that placement of a distal end portion into the patient's urinary bladder will leave a proximal end portion extending beyond the urethral meatus, the distal end portion of the tubular drain body member being preformed so that when unconstrained it forms a bladder retention coil lying in a plane extending at a perpendicular angle to a longitudinal axis of the tubular drain body member, the distal end portion further including at least one aperture extending from a peripheral surface of the tubular drain body member to the lumen through which urine may flow; and a unitary tubular stiffening device insertable into the lumen of the elongated, flexible tubular drain body member and being sufficiently rigid to render the bladder retention coil rectilinear to facilitate insertion of the tubular drain body member into the patient's urethra, the tubular stiffening device having an effective length less than the length of the tubular drain body member and an open distal end and an unobstructed internal lumen for permitting urine flow therethrough as a signal to provide an indication when the distal end portion of the tubular drain body member has been inserted into the patient's urinary bladder, removal of the tubular stiffening device from the lumen of the tubular drain body member following receipt of said signal allowing the distal end portion of the tubular drain body member to reform the bladder retention coil.

2. The urethral drain apparatus as in claim 1 and further including a first molded plastic tubular hub affixed to the proximal end of the tubular drain body member and a second molded tubular hub affixed to the proximal end of the tubular stiffening device, the first and second hubs including means for releasably locking the second hub to the first hub upon the tubular stiffening device being fully inserted into the lumen of the tubular drain body member.

3. The urethral drain apparatus of claim 2 wherein the distal end of the tubular body member is closed and rounded.

4. The urethral drain apparatus of claim 3 wherein the tubular drain body member is void of any apertures in a first zone thereof spanning the patient's bladder neck region when the bladder retention coil is resident in the patient's urinary bladder.

5. The urethral drain apparatus of claim 4 and further including at least one further aperture extending through the tubular drain body member and in fluid communication with the lumen of the tubular drain body member in a second zone proximal of the first zone, the second zone spanning a male patient's prostate gland when the bladder retention coil is resident in the patient's urinary bladder.

6. The urethral drain apparatus of claim 1 wherein the tubular body member is a plastic material selected from the group consisting of polyurethane, polyethylene, and silicone rubber.

7. The urethral drain apparatus as in claim 6 wherein the plastic material has a durometer in a range from about 35 to 90, Shore A.

8. The urethral drain apparatus of claim 1 wherein the distal end portion forming the bladder retention coil includes a plurality of apertures.

* * * * *